Figure 1:
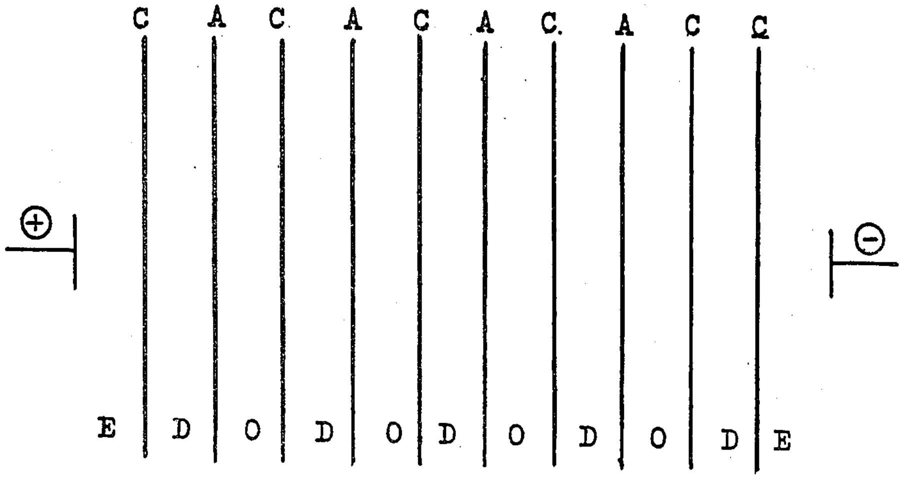

United States Patent [19] [11] 4,375,393
Reiff et al. [45] Mar. 1, 1983

[54] PREPARATION OF DIACETONE-KETOGULONIC ACID

[75] Inventors: Fritz Reiff; Willi Wintermeyer, both of Seeheim-Jugenheim; Rolf Wittmann, Mühltal-Traisa; Jürgen Butzke, Dieburg; Peter Müller, Darmstadt-Arheilgen, all of Fed. Rep. of Germany

[73] Assignee: Merck Patent Gesellschaft mit Beschrankter Haftung, Darmstadt, Fed. Rep. of Germany

[21] Appl. No.: 266,786

[22] Filed: May 26, 1981

[30] Foreign Application Priority Data

May 27, 1980 [DE] Fed. Rep. of Germany ....... 3020104

[51] Int. Cl.[3] ............ C25B 3/02

[52] U.S. Cl. ............ 204/79; 204/180 P

[58] Field of Search ............ 204/78, 180 P, 79

[56] References Cited

U.S. PATENT DOCUMENTS 3,496,091 2/1970 McGriff et al. ............ 204/180 P
4,097,346 6/1978 Robertson ............ 204/180 P

*Primary Examiner*—John F. Niebling
*Attorney, Agent, or Firm*—Millen & White

[57] ABSTRACT

A process for preparing diacetone-ketogulonic acid comprises oxidizing diacetonesorbose to diacetone-ketogulonic acid to an extent of about 30–95% by electrochemical oxidation or $O_2$ oxidation; electrodialysing the resultant reaction solution to separate the pure diacetoneketogulonic acid from the unoxidized diacetonesorbose; and recycling the unoxidized diacetone-sorbose to the oxidation step.

8 Claims, 2 Drawing Figures

PREPARATION OF DIACETONE-KETOGULONIC ACID

BACKGROUND OF THE INVENTION

The present invention relates to a process for the preparation of diacetone-ketogulonic acid, a valuable intermediate in the preparation of vitamin C.

In the preparation of diacetone-ketogulonic acid, the starting material generally is diacetonesorbose. This can be oxidized to diacetone-ketogulonic acid, for example with inorganic oxidizing agents, such as $HNO_3$, $H_2O_2$ or hypochlorite. Catalyzed oxidation with air or oxygen-containing gases, and also electrochemical oxidation, have recently aroused particular interest. In these processes, very good conversions are achieved at the start of the reaction, but the reaction becomes progressively slower as the content of the oxidation product increases. To achieve complete conversion of the diacetonesorbose, it is necessary to employ relatively long reaction times and more rigorous conditions. Concomitantly, there is the danger of further oxidation of the already formed diacetone-ketogulonic acid, which leads to a reduction in yield and to undesired by-products.

SUMMARY OF THE INVENTION

It is therefore an object of this invention to provide a process by which diacetone-ketogulonic acid can be prepared with good conversion, in high yields and with a small amount of waste material.

Upon further study of the specification and appended claims, further objects and advantages of this invention will become apparent to those skilled in the art.

These objects have been achieved by this invention by providing a process for preparing diacetone-ketogulonic acid by the electrochemical oxidation or atmospheric oxidation of diacetonesorbose, comprising separating the reaction solution, partially oxidized to the extent of about 30–95%, by electrodialysis, recovering the pure diacetone-ketogulonic acid product and recycling the unoxidized diacetonesorbose to the oxidation.

DETAILED DISCUSSION

There are several advantages of the procedure of this invention. The oxidation proceeds under optimum conditions, with relatively high concentrations of the starting material. The previous expensive oxidation of the remainder to give 100% conversion of the starting material is obviated, although, of course, the recycling of the unoxidized diacetonesorbose ultimately gives 100% conversion. In a preferred embodiment of the process, both the oxidation and the separation of the diacetone-ketogulonic acid are carried out continuously.

The initial oxidation of the diacetonesorbose, involves processes which are in themselves known. Atmospheric oxidation catalyzed by noble metals is described, for example, in German Patent Specification No. 935,968, Hungarian Patent Specification No. 162,772 and German Offenlegungsschrift No. 2,123,621 and electrochemical oxidation is described, for example, in Tetrahedron 28, 37–42 (1972), Elektrochimia 6, 897–909 (1972), German Offenlegungsschrift No. 1,668,203 or German Offenlegungsschrift No. 2,505,911. The disclosures of all of these references are incorporated by reference herein. Unless specified otherwise herein, details of the oxidation steps are conventional as discussed therein.

For instance, according to these processes about 5 to 15% strength solutions of diacetonesorbose are used. These are brought to a pH of about 12 to about 14 with an alkali metal hydroxide solution, preferably sodium hydroxide solution. This pH is generally kept constant by the further addition of alkali during the course of the reaction which proceeds with the formation of the diacetone-ketogulonic acid.

In contrast to the known processes, however, the oxidation in the process of this invention is not carried out to give a maximum conversion, but only to give a conversion of about 30–95%, preferably 50–85% of the starting material. The oxidation solution, which contains about 6 to 65 g of diacetonesorbose, 65 to 130 g of diacetone-ketogulonic acid and 10 to 30 g of NaOH per kg of solution, is then fed to the dialysis unit.

For this purpose, customary electrodialysis units are used. Therein, a series of cation- and anion-exchange membranes are arranged alternately, either individually or in groups. Typical membrane arrangements are shown in FIGS. I and II. In these figures, A and C denote the anion- and cation-exchange membranes. D and O are the compartments for the dialysate and oxidation solution or dialysis residue. E denotes the electrode compartments.

The solution originating from the oxidation is recirculated by means of a pump through the compartments denoted by O, which are separated from the dialysate compartments D by one cation-exchange membrane and one anion-exchange membrane. On applying a direct-current voltage to the electrodes, electrically charged particles migrate through the membranes into the dialysate solution. Both the oxidation solution and the dialysate solution are recirculated by means of a pump in order to keep the concentration overvoltage at the membranes as low as possible. The circulation rate is highly dependent on the number and geometry of the compartments, but the circulation rate is generally adjusted so that flow velocities along the membranes of about 0.1 to about 0.3 meter/second are achieved.

An electrode solution which serves only to maintain an appropriate conductivity, and also gas and heat transfer, is recirculated in both the electrode compartments by means of a pump. The electrode solution can therefore contain, for example, electrolytes, such as, for example, sodium sulphate or NaOH. The direct-current voltage to be applied to the electrodes depends on the salt content of the solutions in the individual compartment segments. As a rule, a voltage of about 0.5 to about 1.5 volts per cell is applied at the start of the dialysis, and this can increase to about 2 to about 4 volts per cell towards the end. The temperature of the solutions is not in itself critical, but temperatures which are above room temperature to about 75° C. are preferred to influence the viscosity and conductivity of the solutions in an advantageous manner. Typical dialysis times are 2–20 hours.

Any membranes which are based on the principle of cation- and anion-exchange, and the permeability of which is sufficiently high to allow the relatively bulky molecules of diacetone-ketogulonic acid to pass through, can be used. Examples of suitable membranes include those based on polymeric ion exchangers, such as, for example, the Selemion types of Asahi Glass or the Neosepta types from Tokyama Soda or similar membranes from Ionics and Du Pont. Details of all of the dialysis procedures described herein are fully conventional unless specified otherwise and may be found, e.g., in A. T. Kuhn, Industrial Electrochemical Processes, Elsevier Publishing Co., 1971, pages 467–496, whose disclosure is incorporated by reference herein.

In this separation of the diacetone-ketogulonic acid, it has been discovered, surprisingly, that, during the electrodialysis of the alkaline solution containing diacetone-sorbose and diacetone-ketogulonic acid, fractionation occurs whereby, virtually exclusively, NaOH initially passes into the dialysate. It is not until the NaOH content is relatively low that diacetone-ketogulonic acid also passes into the dialysate to an increasing extent. This makes it possible to selectively recover the hydroxide solution, added during the oxidation to neutralize the formed diacetone-ketogulonic acid, and to reuse it. Considerable amounts of alkali metal hydroxide solution and also considerable amounts of acid, which would otherwise be required for neutralizing this hydroxide solution during the precipitation of diacetone-ketogulonic acid, are thereby saved. There is no pollution of the effluent by the salts otherwise obtained during this neutralization. This is a significant contribution to protection of the environment.

Fractional dialyses of this type can be carried out either discontinuously or continuously in at least two dialysis devices connected in series.

The sodium hydroxide solution obtained as the dialysate in the first dialysis step can be recycled directly to the oxidation step. The dialysis residue from the first dialysis step, which only contains small amounts of NaOH, for example about 0–2% by weight, but virtually the whole amount of unoxidized diacetonesorbose and diacetone-ketogulonic acid product, is fed to the second dialysis step. The first step typically is run for 1–5 hours and the second for 5–20 hours. The dialysate obtained from the second step is a solution which contains the remaining sodium hydroxide solution and the bulk of the diacetone-ketogulonic acid and also a little diacetonesorbose, which, solely because of its osmotic pressure, diffuses into the dialysate in small amounts.

The pH value of the dialysis residue is kept at about 7–8 at the end of the dialysis by the addition of NaOH. It contains, except for small losses which have passed into the dialysate, the whole amount of diacetonesorbose and in addition, if appropriate, also a residual concentration of diacetone-ketogulonic acid.

As mentioned, it can be advantageous not to separate the diacetone-ketogulonic acid completely from the oxidation solution. The reason is that the efficiency of the dialysis in respect of diacetone-ketogulonic acid becomes increasingly unfavorable as the concentration of diacetone-ketogulonic acid decreases. The dialysis is therefore preferably interrupted when the residual content of diacetone-ketogulonic acid in the oxidation solution is about 1 to about 25% of the initial amount. Of course, there is no attendant loss of diacetone-ketogulonic acid because the dialysis residue is fed first to the oxidation and then back to the dialysis.

The dialysate from the second dialysis step is fed to the precipitation of the diacetone-ketogulonic acid, which can be effected in the customary manner by acidification with hydrochloric acid; isolated; and processed further to make vitamin C.

The invention thus provides a process which makes it possible to obtain diacetone-ketogulonic acid, which is particularly valuable as an intermediate in the preparation of vitamin C, by virtually complete conversion of diacetonesorbose, with very small amounts of reagents and correspondingly slight waste problems.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the following examples, Selemion membranes of the CMV and AMV type from Asahi Glass are used. However, equally good success can also be obtained using, for example, the ASV types of membrane from Asahi Glass or the 103 PZL 183, 61 AZL 183, CR 61 MZL 183, CR 61 CYL 183 and 103-QZL-219 types from Ionics Inc., and also other membranes, such as, for example, the Neosepta CL-25T, CH-45T, AV-4T, AF-4T or AVS-4T types from Tokyama Soda or the Nafion 152 E, 214, 315 and 427 types from Du Pont.

EXAMPLE 1

In a membrane arrangement corresponding to FIG. I, 71.6 kg of an alkaline solution of diacetoneorbose, partially oxidized electrochemically to the extent of about 63% and consisting of 1.876 kg of NaOH, 3.44 kg of diacetonesorbose and 6.1 kg of diacetone-ketogulonic acid, is circulated through the oxidation solution compartments O by means of a pump. A mixture of 25 kg of fully deionized water and 400 g of 32% strength by weight sodium hydroxide solution is likewise circulated in the separate circulation of the dialysate compartments D. As a third circulation, a 10% strength sodium sulphate solution is pumped through the electrode compartments E.

After an operating time of 4 hours at a direct-current voltage of 13.5 volts, and, at the start of the dialysis, with a current of 40 amperes, 28.7 kg of dialysate solution I, containing 1.09 kg of NaOH (51.21% of the amount used), is drawn off and replaced by a mixture of 25 kg of fully deionized water with 100 g. of 32% strength by weight sodium hydroxide solution. After further electrodialysis at a voltage which increases to 30 volts at the end and with a current which decreases to 5.6 amperes at the end, 50.8 kg of oxidation solution, containing 3.3 kg of diacetonesorbose (96% of the amount used) and 0.55 kg of diacetone-ketogulonic acid (9.0% of the amount used), is drawn off.

43.5 kg of solution, containing 5.524 kg of diacetone-ketogulonic acid (90.7% of the amount used), 0.087 kg of diacetonesorbose (2.5% of the amount used) and 0.864 kg of NaOH (46.0% of the amount used), is obtained as the dialysate II.

EXAMPLE 2

A diacetonesorbose solution, partially oxidized electrochemically to the extent of 55.5% and containing 1.44 kg of sodium hydroxide solution, 2.8 kg of diacetonesorbose and 3.5 kg of diacetone-ketogulonic acid, is dialysed in a manner corresponding to Example 1. The following yields are obtained:

Dialysate I: 1.30 kg of NaOH (90.2% of the amount used).

Dialysate II: 0.36 kg of diacetonesorbose (12.86% of the amount used), 2.96 kg of diacetone-ketogulonic acid (84.6% of the amount used) and 0.116 kg of NaOH (8.05% of the amount used).

Dialysis residue: 2.4 kg of diacetonesorbose (85.7% of the amount used) and 0.5 kg of diacetone-ketogulonic acid (14.3% of the amount used).

EXAMPLE 3

44 kg of a diacetonesorbose solution, partially oxidized electrochemically to the extent of 85.7% and containing 0.88 kg of diacetonesorbose, 5.28 kg of diacetone-ketogulonic acid and 0.792 kg of NaOH, is electrodialyzed as described in Example 1.

After 4 hours at a voltage of 13 volts and with an initial current of 40 amperes, 29.3 kg of dialysate I, containing 0.015 kg of diacetonesorbose (1.7% of the amount used), 0.67 kg of diacetone-ketogulonic acid (12.7% of an amount used) and 0.946 kg of NaOH (99.62% of the amount used), is drawn off and replaced by 25 kg of fully deionized water. After a further 11 hours at a voltage of between 13 and 18.6 volts and with a current of 9–11 amperes, the electrodialysis is ended and the following solutions obtained: 32.5 kg of dialysis residue containing 0.81 kg of diacetonesorbose (92% of the amount used) and 1.33 kg of diacetone-ketogulonic acid (25.2% of the amount used). 35.3 kg of dialysate II containing 0.06 kg of diacetonesorbose (6.81% of the amount used) and 3.21 kg of diacetone-ketogulonic acid (60.8% of the amount used).

EXAMPLE 4

In an electrodialysis cell with a total membrane area of 40 $cm^2$, 250 ml of a solution containing 5 g of diacetonesorbose, 24.8 g of diacetone-ketogulonic acid and 4.35 g of NaOH is dialysed in the course of 6.25 hours, the initial current density of 260 $A/m^2$ dropping to 175 $A/m^2$. The pH value of the solution is kept constantly at about 13 by the addition of NaOH. 301 g of dialysate I, containing 3.7 g of NaOH. (85% of the amount used), 0.1 g of diacetonesorbose (2% of the amount used) and 0.7 g of diacetone-ketogulonic acid (2.8% of the amount used) is obtained.

In a second dialysis step with a current density dropping from 175 $A/m^2$ to 110 $A/m^2$, 323 g of dialysate II, containing 0.13 g of diacetonesorbose (2.6% of the amount used) and 16 g of diacetone-ketogulonic acid (64.5% of the amount used), is obtained.

If the electrodialytic separation of the diacetone-ketogulonic acid is repeated with the dialysate II in the same cell with a current density dropping from 80 $A/m^2$ to 30 $A/m^2$, a dialysate III, containing 0.019 g of diacetonesorbose (0.38% of the amount used) and 12.16 g of the diacetone-ketogulonic acid (49% of the amount used), is obtained.

Figure 2:
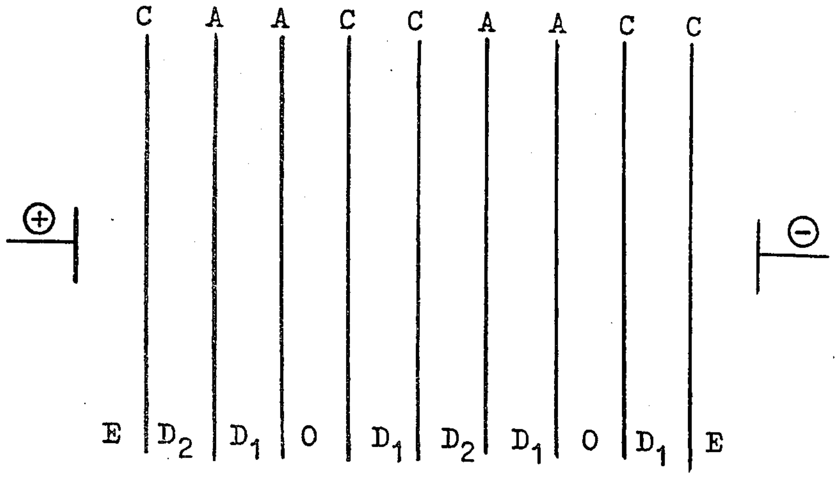

The reduction in the content of the diacetonesorbose in the dialysate containing the diacetone-ketogulonic acid, achieved by the multi-step dialysis in a dialysis arrangement corresponding to FIG. 1, by re-using the dialysate as the original solution and drawing off a depleted dialysate, can also be achieved in a one-step process. A dialysis arrangement corresponding to FIG. 2 is used for this purpose. In this case, the dialysate $D_2$, which, because it has passed through the exchange membranes twice has a greatly reduced content of the diacetonesorbose carried through by diffusion, is removed as the dialysate.

EXAMPLE 5

In an electrodialysis cell with a membrane area of 175 $cm^2$, 0.5 liter of a solution containing 16.5 g of diacetonesorbose, 51.5 g of diacetone-ketogulonic acid and 10.6 g of NaOH is separated in 15 hours. The following are obtained:

In the dialysate I: 8.2 g of NaOH (77.4% of the amount used) with small amounts of diacetonesorbose and diacetone-ketogulonic acid.

In the dialysate II: 2.0 g of NaOH (93.9% of the amount used), 0.5 g of diacetonesorbose (3.0% of the amount used) and 45.0 g of diacetone-ketogulonic acid (87.0% of the amount used).

In the dialysis residue, 15.5 g of diacetonesorbose (93.9% of the amount used) and 6.5 g of diacetone-ketogulonic acid (1.26% of the amount used).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing diacetone-ketogulonic acid comprising oxidizing diacetonesorbose to diacetone-ketogulonic acid to an extent of about 30–95% by electrochemical oxidation or $O_2$ oxidation; electrodialysing the resultant reaction solution to separate the diacetone-ketogulonic acid from the unoxidized diacetonesorbose; and recycling the unoxidized diacetonesorbose to the oxidation step.

2. A process of claim 1 wherein the oxidation is electrochemical.

3. A process of claim 1 wherein the oxidation is is by $O_2$ in the form of air.

4. A process of claim 1, wherein the oxidation, electrodialysis and recycling are carried out continuously.

5. A process of claim 1 wherein only a portion of the diacetone-ketogulonic acid in the reaction solution is separated off in the electrodialysis and the remainder which is not separated off is recycled to the oxidation step together with the unreacted diacetonesorbose.

6. A process of claim 5 wherein 1–25% of the initial amount of diacetone-ketogulonic acid in the oxidation solution is not separated off in the electrodialysis and is recycled to the oxidation step.

7. A process of claim 1 wherein the electrodialysis is carried out in two stages, in the first of which sodium hydroxide is predominantly separated off and then recycled to the oxidation step, and in the second of which the diacetone-ketogulonic acid is predominantly separated off.

8. A process of claim 1 wherein the electrodialysis is carried out in an apparatus in which a series of cation and anion-exchange membranes are arranged alternately, either individually or in groups.

* * * * *